United States Patent [19]

Becker et al.

[11] Patent Number: 4,596,877

[45] Date of Patent: Jun. 24, 1986

[54] HERBICIDAL CYCLOHEXANONE SUBSTITUTED TETRAHYDRO-THIOPYRAN DERIVATIVES, COMPOSITIONS, AND METHOD OF USE THEREFOR

[75] Inventors: Rainer Becker, Bad Durkheim; Dieter Jahn, Edingen-Neckarhausen; Michael Keil, Freinsheim; Ulrich Schirmer, Heidelberg; Bruno Wuerzer, Otterstadt; Norbert Meyer, Ladenburg, all of Fed. Rep. of Germany

[73] Assignee: BASF Aktiengesellschaft, Fed. Rep. of Germany

[21] Appl. No.: 655,727

[22] Filed: Sep. 28, 1984

[30] Foreign Application Priority Data

Sep. 30, 1983 [DE] Fed. Rep. of Germany ....... 3335455
Apr. 5, 1984 [DE] Fed. Rep. of Germany ....... 3412794

[51] Int. Cl.$^4$ .................... A01N 43/18; C07D 335/02
[52] U.S. Cl. ............................................. 71/90; 549/13
[58] Field of Search ................................ 549/13; 71/90

[56] References Cited

U.S. PATENT DOCUMENTS 4,422,864 12/1983 Becker et al. .................... 549/13

FOREIGN PATENT DOCUMENTS 0115808 2/1983 European Pat. Off. ............ 549/28

OTHER PUBLICATIONS

U.S. patent application Ser. No. 750,997, filed 7/3/85.

Primary Examiner—Henry R. Jiles
Assistant Examiner—J. G. Mullins
Attorney, Agent, or Firm—Keil & Weinkauf

[57] ABSTRACT

Cyclohexenone derivatives of the formula

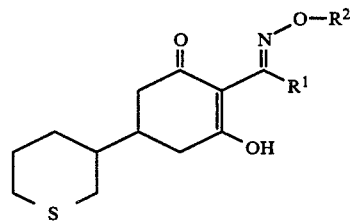

where $R^1$ is alkyl and $R^2$ is chloroalkenyl are useful in controlling undesirable plant growth.

7 Claims, No Drawings

HERBICIDAL CYCLOHEXANONE SUBSTITUTED TETRAHYDRO-THIOPYRAN DERIVATIVES, COMPOSITIONS, AND METHOD OF USE THEREFOR

The present invention relates to cyclohexenone derivatives and to herbicides which contain these compounds as active ingredients.

It is known that cyclohexene-1,3-dione derivatives with heterocyclic substituents in the 5-position and haloalkenyloxyamino-alkylidene radicals in the 2-position are herbicidally active (European Published Application No. 0,071,707). 5-Tetrahydrothiopyranyl-cyclohexanedione derivatives with haloalkenyl radicals as oxime-ether substituents have however not previously been disclosed.

We have found that cyclohexenone derivatives of the formula

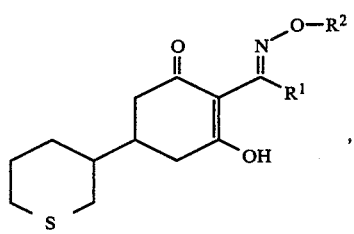

where $R^1$ is $C_1$–$C_4$-alkyl and $R^2$ is $C_3$–$C_5$-chloroalkenyl, and their salts, possess excellent herbicidal activity.

The compounds of the formula I can exist in tautomeric forms, all of which are embraced by what we claim.

In the general formula I, $R^1$ is methyl, ethyl, n-propyl, i-propyl, n-butyl, s-butyl, t-butyl or i-butyl and $R^2$ is a $C_3$–$C_5$-alkenyl radical bearing 1-3 chlorine atoms, eg. cis-3-chloroallyl, trans-3-chloroallyl, cis-3-chlorobut-2-enyl, trans-3-chlorobut-2-enyl, 2-chloroallyl or 2,3,3-trichloro-prop-2-enyl.

Preferred cyclohexenone derivatives of the formula I are those where $R^2$ is 3-chloro-prop-2-enyl. Preferred radicals $R^1$ are methyl, ethyl and propyl, more especially the last two.

Suitable salts of the compounds of the formula I are the alkali metal salts, especially the potassium or sodium salts, alkaline earth metal salts, especially calcium, magnesium or barium salts, manganese, copper, zinc and iron salts, and ammonium and phosphonium salts, for example alkylammonium, dialkylammonium, trialkylammonium or tetraalkylammonium salts, benzyltrialkylammonium salts, triphenylphosphonium salts, trialkylsulfonium salts or trialkylsulfoxonium salts.

The compounds of the formula I may be obtained by reacting a compound of the formula (II)

where $R^1$ has the above meanings, with a hydroxylamine derivative $R^2O$—$NH_3Y$, where $R^2$ has the above meanings and Y is an anion.

The reaction is advantageously carried out in a heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides or oxides of alkali metals or alkaline earth metals, especially of sodium, potassium, magnesium and calcium.

Moreover, organic bases, such as pyridine or tertiary amines, may be used.

The reaction proceeds particularly well at a pH of from 2 to 9, especially from 4.5 to 5.5. The pH is advantageously adjusted by adding an acetate, for example an alkali metal acetate, especially sodium acetate or potassium acetate or a mixture of both. The alkali metal acetate is added in amounts of, for example, from 0.5 to 2 moles per mole of the ammonium compound of the formula $R^2O$—$NH_3Y$.

Examples of suitable solvents are dimethylsulfoxide, alcohols, eg. methanol, ethanol and isopropanol, benzene, hydrocarbons and chlorohydrocarbons, eg. chloroform, dichloroethane, hexane and cyclohexane, es-

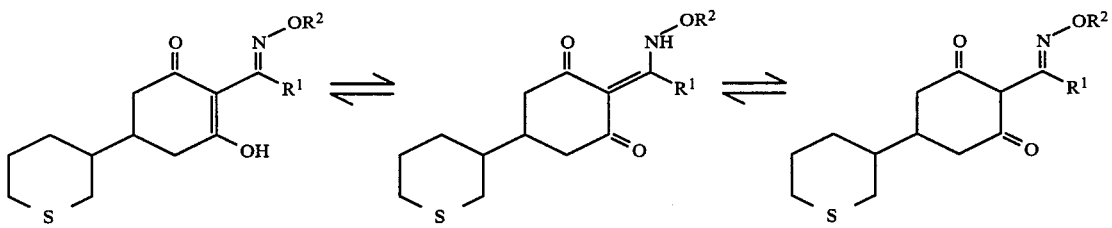

ters, eg. ethyl acetate, and ethers, eg. dioxane and tetrahydrofuran.

The reaction is completed after a few hours, and the reaction product can then be isolated by concentrating the mixture, adding water, extracting with a non-polar solvent, such as methylene chloride, and distilling off the solvent under reduced pressure.

The compounds of the formula I may moreover be obtained by reacting a compound of the formula II with a hydroxylamine of the formula $R^2O$—$NH_2$, where $R^2$ has the above meanings, in an inert diluent at between 0° C. and the boiling point of the reaction mixture, especially between 15° and 70° C. If desired, the hydroxylamine can be employed in the form of an aqueous solution.

Examples of suitable solvents for this reaction are alcohols, eg. methanol, ethanol, isopropanol and cyclohexanol, hydrocarbons and chlorohydrocarbons, eg. hexane, cyclohexane, methylene chloride, toluene and dichloroethane, esters, eg. ethyl acetate, nitriles, eg. acetonitrile, and cyclic ethers, eg. tetrahydrofuran.

The compounds of the formula I can also be prepared by reacting a compound of the formula II with an unsubstituted hydroxylammonium salt NH$_2$OH.HY, where Y has the above meaning, to give a corresponding oxime, which is then O-alkylated. In this process, it is necessary to take account of the tendency of the oxime, formed as an intermediate, to undergo undesirable cyclization reactions; this tendency can be influenced by suitable auxiliaries and suitable reaction conditions.

Suitable solvents are those mentioned for the reaction of a compound of the formula II with a hydroxylamine, and suitable auxiliary bases are those mentioned for the reaction of a compound of the formula II with a hydroxylamine derivative of the formula R$^2$—O—NH$_3$Y, though twice the amount of base is required.

The alkali metal salts of the compounds of the formula I can be obtained by treating these compounds with sodium hydroxide or potassium hydroxide in aqueous solution or in an organic solvent, eg. methanol, ethanol or acetone. A sodium alcoholate or potassium alcoholate can also serve as the base.

The other metal salts, eg. the manganese, copper, zinc, iron, calcium, magnesium and barium salts, can be prepared from the sodium salts by reaction with the corresponding metal chlorides in aqueous solution. Ammonium, phosphonium and sulfonium salts can be prepared by reacting a compound of the formula I with an ammonium, phosphonium, sulfonium or sulfoxonium hydroxide, if appropriate in aqueous solution.

The compounds of the formula II can be prepared from cyclohexane-1,3-diones of the formula IV, which can also be present in the tautomeric form IVa

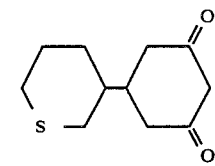

by methods known from the literature (Tetrahedron Letters, 29 (1975), 2491).

It is also possible to prepare a compound of the formula II via the intermediate enol-ester which is formed in the reaction of the compound of the formula IV and undergoes rearrangement in the presence of an imidazole or pyridine derivative (Japanese Laid-Open Specification 79/063052).

The compounds of the formula IV are obtained by methods known from the literature, as illustrated below:

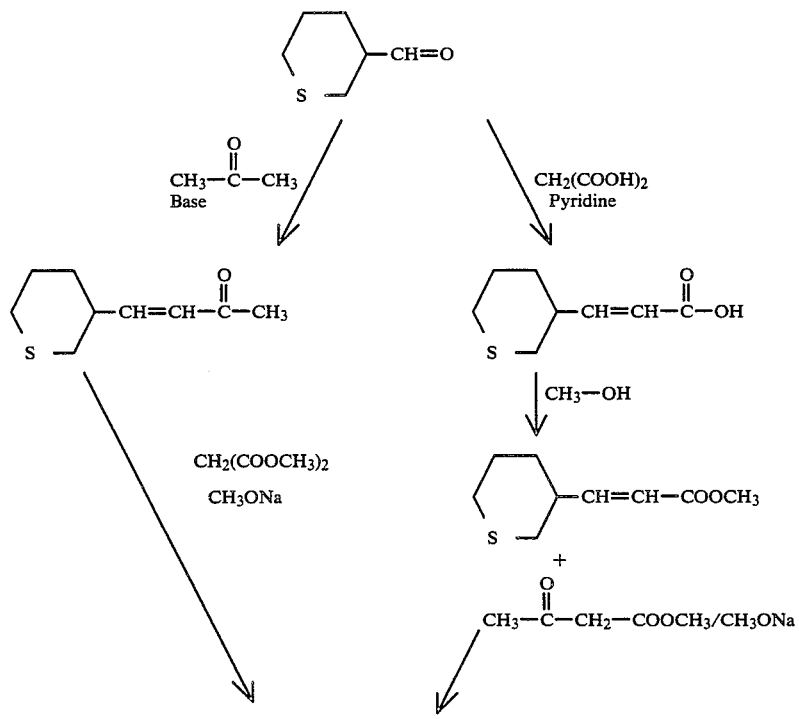

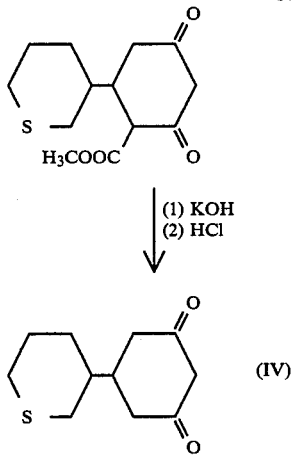

The Example which follows illustrates the preparation of the cyclohexenone derivatives of the formula I. Parts by weight bear the same relation to parts by volume as that of the kilogram to the liter.

EXAMPLE 1

14.1 parts by weight of 2-(n-butyryl)-5-(tetrahydrothiopyran-3-yl)-cyclohexane-1,3-dione are dissolved in 100 parts by volume of methanol, 7.9 parts by weight of O-(trans-3-chloroallyl)-hydroxylamine hydrochloride and 4.6 parts by weight of sodium bicarbonate are added and the mixture is stirred for some hours at room temperature; it is then concentrated, the residue is taken up in methylene chloride and the solution is washed with water and again concentrated. 16.1 parts by weight of an oil of $n_D^{22} = 1.5669$ (Compound No. 1) are left.

The following compounds of the formula I can be prepared analogously:

| Compound No. | R$^1$ | R$^2$ | $n_D$/melting point[°C.]/ $^1$H NMR data (in ppm, based on tetramethylsilane) |
|---|---|---|---|
| 1 | C$_3$H$_7$ | trans-CH$_2$CH=CHCl | 1.5669 (22° C.) |
| 2 | C$_3$H$_7$ | cis-CH$_2$CH=CHCl | 1.5661 (22° C.) |
| 3 | C$_2$H$_5$ | trans-CH$_2$CH=CHCl | 1.5730 (22° C.) |
| 4 | C$_2$H$_5$ | cis-CH$_2$CH=CHCl | 1.5715 (22° C.) |
| 5 | CH$_3$ | trans-CH$_2$CH=CHCl | 57–64 |
| 6 | CH$_3$ | cis-CH$_2$CH=CHCl | 48–50 |
| 7 | n-C$_3$H$_7$ | CH$_2$CCl=CH$_2$ | |
| 8 | C$_2$H$_5$ | CH$_2$CCl=CH$_2$ | |
| 9 | n-C$_3$H$_7$ | trans-CH$_2$CH=CClCH$_3$ | |
| 10 | n-C$_3$H$_7$ | cis-CH$_2$CH=CClCH$_3$ | |
| 11 | C$_2$H$_5$ | trans-CH$_2$CH=CClCH$_3$ | |
| 12 | n-C$_3$H$_7$ | cis-CH$_2$CH=CClCH$_3$ | |
| 13 | n-C$_3$H$_7$ | CH$_2$CCl=CCl$_2$ | 1.5704 (24° C.) |

The cyclohexenone derivatives of the formula I, and their salts, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 13 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 4 is dissolved in mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 3 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 3 is intimately mixed with 97 parts by weight of particulate kaolin. A dust is obtained containing 3% by weight of the active ingredient.

VII. 30 parts by weight of compound no. 6 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 5 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.01 to 3 kg/ha and more, but is preferably from 0.025 to 0.5 kg/ha.

The herbicidal action of the cyclohexenone derivatives of the formula I on the growth of Gramineae and broadleaved crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and transplanted to the pots a few days before treatment. The application rates for postemergence treatment varied from 0.015 to 3.0 kg of active ingredient per hectare. No covers were placed on the pots in this treatment method.

The pots were set up in the greenhouse—species from warmer areas at from 20° to 35° C., and species from moderate climates at 10° to 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Avena sativa, Echinochloa crus-galli, Glycine max., Hordeum vulgare, Lolium multiflorum, Setaria italica, Sinapis alba, Sorghum bicolor, Sorghum halepense, Triticum aestivum, Zea mays, Centaurea cyanus, Cyperus esculentus, Galium aparine, Ipomoea spp., and Mercurialis annua.

The compounds of the formula

disclosed in European Laid-Open Application 00 71 707 were used as comparative agents:

| Compound | $R^1$ | X | Y | Z |
|---|---|---|---|---|
| I | $C_2H_5$ | S | H | H |
| II | $n-C_3H$ | O | $CH_3$ | Cl |
| III | $n-C_3H_7$ | O | H | Cl |

PREEMERGENCE APPLICATION

On preemergence application, for example compounds nos. 1, 2 and 4, applied at a rate of 3.0 kg/ha, were herbicidally effective on plants from the Gramineae family; the broadleaved test plant Sinapis alba remained undamaged.

POSTEMERGENCE APPLICATION

On postemergence application, for example compound no. 1, at 0.06 kg/ha, had a herbicidal action far superior to that of comparative agent II, and, at 0.125 kg/ha, a herbicidal action far superior to that of comparative agent III, on plants from the Gramineae family. Soybean plants remained undamaged. Compound no. 3, at 0.015 kg/ha, was stronger than comparative agent I on grasses such as Echinochloa crus-galli or Sorghum bicolor (as volunteer millet or shattercane). On postemergence application of 0.125 kg/ha this compound had a much stronger action on wheat (which may also occur as an unwanted grass) than comparative agent I, and was also tolerated by soybeans.

By comparison, compounds nos. 2 and 4, at 0.06 kg/ha, damaged wheat (Triticum aestivum, "Vuka" variety) only slightly; they can therefore be considered to be selective in this crop, whereas comparative agent III caused considerable damage. The compounds are also tolerated by broadleaved crops.

At an application rate of 3.0 kg/ha, compounds nos. 5,6 and 13 had an excellent action on species from the Gramineae family. Compounds nos. 5 and 6 also had a considerable action on Cyperus esculentus and broadleaved weeds selected by way of example.

In view of the numerous application methods possible, the cyclohexenone derivatives of the formula I may be used in a further large number of crops for removing unwanted wild grasses or grassy crop plants growing where they are not desired.

The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |

| Botanical name | Common name |
| --- | --- |
| *Vigna sinensis (V. unguiculata)* | cow peas |
| *Vitis vinifera* | grapes |
| *Zea mays* | Indian corn, sweet corn, maize |

To increase the spectrum of action and to achieve synergistic effects, the cyclohexenone derivatives of the formula I may be mixed and applied together with numerous representatives of other herbicidal or growth-regulating active ingredient groups. Examples of suitable mixture components are diazines, 4H-31-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexenone derivatives having a different structure, etc.

It may also be useful to apply the novel compounds, or herbicidal agents containing them, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone derivative of the formula

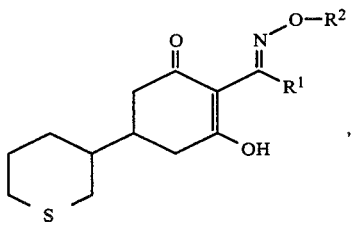

where $R^1$ is $C_1$–$C_4$-alkyl and $R^2$ is $C_3$–$C_5$-chloroalkenyl, or a salt thereof.

2. A cyclohexenone derivative of the formula I as defined in claim 1, where $R^2$ is 3-chloroprop-2-enyl.

3. A cyclohexenone derivative of the formula I as defined in claim 1, where $R^1$ is n-propyl and $R^2$ is trans-3-chloroprop-2-enyl.

4. A herbicidal composition containing inert additives and a herbicidally effective amount of a cyclohexenone derivative of the formula I as defined in claim 1.

5. A herbicidal composition containing inert additives and a herbicidally effective amount of a cyclohexenone derivative of the formula I as defined in claim 2.

6. A process for controlling unwanted plant growth, wherein the unwanted plants and/or the area to be kept free from unwanted plant growth are treated with a herbicidally effective amount of a cyclohexenone derivative of the formula I as defined in claim 1.

7. The process of claim 6, wherein the amount of cyclohexenone derivative of the formula I which is applied is from 0.01 to 3 kg/ha.

* * * * *